US012616796B2

(12) United States Patent
Marcoz

(10) Patent No.: US 12,616,796 B2
(45) Date of Patent: May 5, 2026

(54) INJECTION MONITORING MODULE WITH MAGNETIC ROTATION SENSING

(71) Applicant: BIOCORP PRODUCTION S.A.S., Issosire (FR)

(72) Inventor: Alain Marcoz, Issoire (FR)

( * ) Notice: Subject to any disclaimer, the term of this patent is extended or adjusted under 35 U.S.C. 154(b) by 602 days.

(21) Appl. No.: 18/247,273

(22) PCT Filed: Oct. 13, 2020

(86) PCT No.: PCT/IB2020/000898
§ 371 (c)(1),
(2) Date: Mar. 30, 2023

(87) PCT Pub. No.: WO2022/079462
PCT Pub. Date: Apr. 21, 2022

(65) Prior Publication Data
US 2023/0405233 A1      Dec. 21, 2023

(51) Int. Cl.
*A61M 5/315* (2006.01)

(52) U.S. Cl.
CPC . *A61M 5/31553* (2013.01); *A61M 2205/3317* (2013.01)

(58) Field of Classification Search
CPC .................. A61M 5/31553; A61M 2205/3317
See application file for complete search history.

(56) References Cited

U.S. PATENT DOCUMENTS

| | | | | |
|---|---|---|---|---|
| 2017/0232203 A1* | 8/2017 | Krusell | ................... | A61M 5/24 |
| | | | | 604/207 |
| 2019/0001060 A1 | 1/2019 | Gylleby | | |
| 2020/0147317 A1* | 5/2020 | Olesen | .............. | A61M 5/31525 |
| 2020/0147318 A1 | 5/2020 | Antonelli | | |

FOREIGN PATENT DOCUMENTS

| | | |
|---|---|---|
| JP | 2019524232 A | 9/2019 |
| JP | 2020527424 A | 9/2020 |
| WO | 2013004843 A1 | 1/2013 |

(Continued)

OTHER PUBLICATIONS

ISR; European Patent Office; NL; Jun. 30, 2021.

*Primary Examiner* — Dung T Ulsh
(74) *Attorney, Agent, or Firm* — Patshegen IP; Moshe Pinchas

(57) ABSTRACT

Injection monitoring module removably mountable to a proximal extremity of an injection pen comprising a pen body, a proximally located dose setting wheel, and an injection activator, the dose setting wheel rotating about a central longitudinal axis of the pen during dose setting, the injection monitoring module comprising a hollow main body coaxially mounted on, and engaging in co-rotation with the dose setting wheel, the main body comprising a longitudinal bore having a proximal and distal extremities, and a central longitudinal axis; one or more magnets located on or within the main body; an injection monitoring system comprising at least one magnetic sensor movable in translation along the central axis within the bore, from a first monitoring position, to a second monitoring position; the injection monitoring module further comprising a rotational stop means preventing rotational movement of the monitoring system about the central axis during dose selection.

21 Claims, 5 Drawing Sheets

(56)            References Cited

FOREIGN PATENT DOCUMENTS

| WO | 2014128156 | A1 | 8/2014 |
|----|-----------|----|--------|
| WO | 201713463 | A1 | 7/2015 |
| WO | 201713464 | A1 | 7/2015 |
| WO | 2018138542 | A1 | 1/2017 |
| WO | 2018013419 | A1 | 1/2018 |
| WO | 2019175615 | A8 | 3/2018 |
| WO | 2018064784 | A1 | 4/2018 |
| WO | 2019057911 | A1 | 3/2019 |
| WO | 2019175790 | A1 | 3/2019 |

* cited by examiner

INJECTION MONITORING MODULE WITH MAGNETIC ROTATION SENSING

The present invention relates generally to monitoring systems for injectable drug delivery devices, and in particular to injection monitoring for injection pen systems.

Injection monitoring is a well known field associated with injectable drug delivery devices, especially with regard to infusion systems, for example. Over time, such monitoring systems have been transferred more recently to injection pen systems for delivery of a drug, enabling users of such pen injection systems, and health care professionals involved in the treatment and follow-up of such patients, to monitor more closely their own injection regimes, and in many cases, the doses actually administered, in an attempt to lead to better healthcare outcomes. These developments have been accompanied by the increased associated use of software and portable communications devices such as tablets or smartphones, which have been programmed to receive information from, and interact with, the monitoring systems in order to provide information to the user or healthcare professional on-the-fly, or at regular intervals via appropriate communications units included in the monitoring systems.

In regard to pen injection systems in particular, for example, one of the challenges has been to provide easy to use, reliable and fairly failsafe monitoring systems that can be adapted to the various different variants of such commercially available pen injection systems, of which there are many. Previous attempts at providing such monitoring systems have usually involved adapting the body of the pen injection system by including electronic components therein along with one or more sensors. One of the major disadvantages of such systems however, is that they tend to make the end product, once all of the electronic components have been integrated, into fairly bulky and unwieldy objects, and thus more difficult to use from a user perspective. Additionally, such modified systems tend to be very specific to a given brand or a manufacturer, and thus of little or no use with pen injection devices of other manufacturers. There has furthermore been a tendency to attempt to reduce the overall volume of the injection pen bodies as much of possible through miniaturisation of the complex electronic components, which in turn has brought about its own problems, in particular with regard to electromagnetic interference between the various components due to the close proximities of the circuits providing the required or desired integrated functionality. Moving the sensors in such monitoring systems further away from the source of electromagnetic interference only further complicates matters, potentially leading to erroneous readings, or requiring further systems to compensate for the physical separation of the sensors from the other electronic components, such as a micro-controller designed to control and command the various components and manage their interactions.

The injection pen systems in question are well known per se and are commonly equipped with a proximally located dose setting wheel and injection activator, the dose setting wheel being rotatable about a central longitudinal axis of the pen injection system. The wheel is rotated by the user to select the dose of drug to be administered. The pen is generally configured, either mechanically or electro-mechanically to effect an injection upon activation of an injection activator. Such injection activators are quite commonly a simple press or push-button, in mechanical or electrical contact with the dispensing mechanism located within the pen injection system, the pressing of which causes the injection mechanism to fire and inject the drug contained within the pen injection system. In some pen injector systems, the dose setting wheel is configured to rotate not only during dose setting, but also during injection. This is generally achieved through the inclusion of one or more metallic components, such as a helically wound drive spring located within a housing body of the injection pen system and physically coupled to the dose setting wheel. As such metallic elements are relatively large objects in comparison to the electronic component systems that are included in many pen injection systems today, these large metallic objects can further perturb signals that the sensors in such electronic component systems are designed to capture or pick up, rendering the systems potentially less accurate, and/or requiring that complex correction mechanisms be put in place to avoid calculation errors.

Some attempts at overcoming the difficulties of electronic component integration have already been described in the patent literature.

For example, published PCT patent application WO2014128156A1 relates to a sensor assembly having a first rotary sensor part with a plurality of individual electrically conducting sensor areas arranged in a pattern, a second rotary sensor part arranged rotationally relative to the first part, and comprising a plurality of contact structures adapted to be in contact with conducting sensor areas on the first sensor rotary part. The contact structures are configured to engage and connect different sensor areas as the first and second part of the rotary sensor rotate relative to each, the created connections being indicative of a rotational position between the first and second portions. One of the contact structures is an actuatable contact structure being axially moveable relative to the first portion and having a connected position in which the actuatable contact structure is in contact with a sensor area and a disconnected position in which the actuatable contact structure is not in contact with a sensor area. This system is housed within the pen injector body, at least partly within the volume inside the dose setting wheel. The system also comprises a visual display, such as an LCD display located on, or instead of, the injection activator button.

In comparison, published PCT application WO2018013419A1 relates to a dose detection system including a dosing component attached to an actuator and rotationally and axially moveable relative to a coupling component attached to a dose setting member, and comprising a module including an electronic sensor operative to detect a relative rotation of the coupling component and the dosing component to detect a dose delivered by the medication delivery device. The dose detection module is removably coupled to a proximal end of a pen injection system, and is intended to function as a means to detect the amount of medication dispensed by the pen injection system while attached thereto, store the detected dose in memory, and transmit a signal representative of the detected dose to a remote communication device. The system comprises a pair of rotatable and translatable cylinders that interact with each other via electrical contacts provided on the cylinder surfaces to denote various states or positions of the injection administration process including dose setting, the electrical contacts being connected to a collection of electronic components housed on a flexible printed circuit board, disposed in an accordion-style arrangement of superimposed folds within the removably couple body, and which is insulated between the overlapping layers of circuit board by an electrically non-conducting spacer layer to prevent potential electric, electronic and electromagnetic interference.

One immediate observation of the above-described configuration is that despite the use of a folded flexible printed circuit board to provide multiple surfaces on which to position the electronic components, their relative spatial density and positioning with regard to each other has necessitated that non-conducting spacers be provided between the layers of electronic componentry. The immediate consequence of this is an increased height in the module and a necessarily increased complexity of the clip-on dose detection module described therein.

Furthermore, various other injection monitoring modules for injection pen systems are also known from published PCT applications WO2019/175790, WO2019175615, WO2018138542, WO2017013464, and WO2017013463.

Accordingly, one object of the present invention is to provide an injection monitoring module adapted and configured to be removably attached to a proximal extremity of an injection pen system for delivery of a drug, the injection pen system having a dose setting wheel that can be rotated about a central longitudinal axis of the pen injection system for setting a dose of drug to be injected, and optionally fixed against rotation during injection, whilst obviating the need for complicated shielding or protecting solutions to counter any unwanted electrical, electronic, or electromagnetic effects caused by the relatively high density of the electronic components within the monitoring module.

Another object of the present invention is to provide an injection monitoring module as above, wherein said monitoring module is adapted and configured to determine a dose that has been set, and an injection begin point. For the purposes of the present invention, the expression "injection begin point" as used herein signifies the point at which the injection mechanism within the pen is activated. This usually occurs by moving an injection activator, such as a push button located on the proximal extremity of the pen injection system, in a distal direction.

Yet another object of the invention is to provide an injection monitoring module as above, in which said module is adapted and configured to detect or calculate a dose or amount set by a user of injectable substance contained within the pen injection system, an injection begin or start point, and an injection end point in said pen injection system, and therefrom determine whether or not all of the dose or amount of injectable substance set by the user of the pen injection system has been ejected from said pen system.

These and other objects of the invention will become readily apparent from the complete reading of the current specification.

According to any of the above objects therefore, there is provided an injection monitoring module adapted and configured to be removably mounted to a proximal extremity of an injection pen system for delivery of a drug, the injection pen system having a pen body, a proximally located dose setting wheel connected to said body, and an injection activator, the dose setting wheel being rotatable about a central longitudinal axis of the pen injection system during dose setting, wherein the injection monitoring module comprises:

a hollow main body adapted and configured to be coaxially mounted on, and engage in co-rotation with, the dose setting wheel at the proximal extremity of the injection pen system, the hollow main body comprising a central longitudinal bore having a proximal extremity and a distal extremity, and a central longitudinal axis;

a magnetic field production means, located on or within the hollow main body, at the proximal extremity of the central longitudinal bore;

an injection monitoring system comprising at least one or a plurality of magnetic sensors, the injection monitoring system being located at the proximal extremity of, and movable in translation along said central longitudinal axis within the bore of the hollow main body, from a first monitoring position in which the injection monitoring system is not in abutting contact with a proximal surface of the injection activator, to a second monitoring position in which the injection monitoring system is in abutting contact with a proximal surface of the injection activator; the injection monitoring module further comprising a rotational stop means configured and adapted to prevent rotational movement of the injection monitoring system about said central longitudinal axis during dose setting.

As used herein, the terms "pen injection system" and "injection pen system" are used interchangeably to designate a generally handheld pen-shaped injection system, such systems being readily well known per se and commercially available for use in the treatment of many various medical indications. These systems are also often generally designed for self-injection of a drug by the user in need of treatment for the given medical indication. This is for example the case with insulin, supplied in various forms for use in the treatment of diabetes, for example the pen injection systems commercialized under the brand names FlexPen®, as commercialized by Novo Nordisk, Kwikpen®, as commercialized Eli Lilly, or Lantus Solostar®, as commercialized by Sanofi, being but three of the most well known. Other drugs are also used with this category of medical devices, and are required, for example, to address potentially life-threatening situations, enabling immediate emergency injection of a required drug, such as anaphylactic shock treatments, anticoagulants, opioid receptor agonists and antagonists, and the like, to the extent that it has become a common occurrence for patients suffering from, or susceptible to, such ailments to carry these devices around with them.

The injection pen system, to which the injection monitoring module according to the invention is adapted and configured for removable attachment, is equipped with a proximally located dose setting wheel and an injection activator. The dose setting wheel rotates about a central longitudinal axis of the pen injection system to allow a user to set the dose of medicament for injection. During the dose setting, or dose "dialling" step, the dose setting wheel is generally rotatable in both a clockwise, and a counter-clockwise direction, these directions corresponding generally to an increase in the selected dose, and a decrease in the selected dose, to be administered, respectively, or vice-versa, depending on the manufacturer. The injection activator is often represented by a push-button, usually located proximally of the dose setting wheel, and in the majority of injection pens at the proximal extremity of the injection pen system. After a dose has been set, or "dialled", as the term is commonly known in the art, when a user of the injection system then presses the injection activator in a distal direction, a piston is driven which is connected to a plunger in order to expel drug from a chamber within the injection pen body out through a needle that the user has inserted into an appropriate injection site, for example, the skin, fatty tissue, or muscle, depending on the type of drug to be administered. The dose setting wheel is sometimes, but not necessarily, also coupled to the injection drive mechanism so that it can, depending on the manufacturer and model of injection pen, also rotate as injection of the drug proceeds. The functioning of such injection systems is well known per se in the art. The monitoring module as envisaged according to the present invention is intended for mounting onto a pen injection system in which the dose setting wheel can be configured to either rotate during the ejection/injection phase of operation, or, on the contrary, not rotate during the ejection/injection phase of operation of the pen injection system. For example, the Kwikpen® injection pen mentioned above does not have a dose setting wheel that rotates during injection, whereas the dose setting wheel of the Lantus Solostar® and and FlexPen® injection pens do rotate during injection.

The injection monitoring module according to the invention, therefore, is adapted and configured to be removably attached to a proximal extremity of such an injection pen system. The expressions "removably attached", "removably attachable", "removably mounted" or "removably mountable" as might be used in the present specification are to be understood as referring to the possibility of attaching, or mounting, and subsequently removing, the injection monitoring module, for example, in the case of transferring the injection monitoring module to another pen injection system, or for example, if the monitoring module is damaged during use and requires replacement. Such attachment and subsequent removability can be achieved by providing coupling means on the monitoring module which engage in a releasable manner with the proximal extremity of the pen injection system, for example via frictional or elastic engagement, or via other releasable fastening means, such as clips, straps, screw threads and corresponding tightening rings, and the like, which engage with either the dose setting wheel, or the injection activator, and/or even the body of the pen injection system.

The rotational stop means mentioned above are to be understood as means by which rotation of the injection monitoring system around the central longitudinal axis is physically prevented during dose setting/dose dialling, and optionally advantageously, also when the injection monitoring system is moved from the first injection monitoring position to the second injection monitoring position, and vice-versa, that is, when the injection monitoring system is moved from the second monitoring position back to the first injection monitoring position.

The advantage of providing such a rotational stop means in an injection monitoring module as envisaged by the invention is that the setting, or "dialling" of the dose in the first injection monitoring position will be identified by the injection monitoring system as being the selected dose, whereas such an identification of the dialled dose being the selected dose would not necessarily be correct if the injection monitoring system was allowed to rotate, for whatever reason, during the dialling of a dose through rotation of the dose setting wheel. A further advantage of such a rotationally blocked, or stopped, monitoring module as provided for by the present invention, during selection of the dose to be ejected, is that on subsequent injection, it does not actually matter whether the injection monitoring system rotates, whether accidentally or by design, thereby eliminating the need for any other corrective measures for the determination of the selected dose, which might otherwise have been necessary.

According to one object therefore, the rotational stop means comprises a rotationally fixed coupling disposed in parallel to the central longitudinal axis, the rotationally fixed coupling connecting the injection monitoring system to the body of the pen injection system. The rotationally fixed coupling is configured and adapted to prevent rotation of the injection monitoring system about the central longitudinal axis, during dose setting or dialling, but also more generally, and advantageously, as the injection monitoring system translates from the first monitoring position to the second monitoring position, and further advantageously, as the injection monitoring system translates from the second monitoring position back to the first monitoring position. In this way, one can ensure that no rotation of the injection monitoring system will occur, whether accidentally or deliberately, but particularly not during dose selection or dose dialling, and advantageously also not during injection of the dialled dose, nor furthermore after completion of injection, when the user releases digital pressure on the injection activator cap of the injection monitoring system.

According to yet another object, the rotational stop means is further configured and adapted to permit translational movement of the injection monitoring system from the first injection monitoring position to the second injection monitoring position during injection, and vice-versa, that is to say, from the second injection monitoring position to the first injection monitoring position.

According therefore to yet another object, the rotationally fixed coupling comprises:

at least one elongate rod member, or a plurality of elongate rod members, extending from the injection monitoring system in a distal direction in parallel to the longitudinal axis and bypassing an outside surface of the hollow main body; and a sheath member, mounted on the body of the injection pen system, adapted and configured to receive the at least one, or plurality of, elongate rod members in sliding engagement with said sheath member during translational movement of the injection monitoring system from the first monitoring position to the second monitoring position.

It will be understood from the above that the elongate rod member, and corresponding sheath member, cooperate with each other to permit sliding engagement of the elongate rod member within the sheath member as the injection monitoring system is moved from the first injection monitoring position to the second injection monitoring position, but also vice-versa, that is to say, from the second injection monitoring position back to the first injection monitoring position. The sliding engagement between the elongate rod member and the sheath member occurs substantially in parallel to the central longitudinal axis.

As mentioned above, the at least one elongate rod member, or plurality of said elongate rod members extend from the injection monitoring system in a distal direction, that is to say, in direction away from the proximal extremities of both the injection pen system and the injection monitoring module, and in parallel to the central longitudinal axis. Said rod member, or rod members, is/are furthermore located outside of an outside surface of the hollow main body, and is/are shaped and dimensioned to bypass the hollow body on the outside thereof, and therefore does/do not interfere with the dose setting functionality of said hollow body, which is required to rotate in order to be able to set a dose on the pen injection system through co-rotating contact with the dose setting wheel. Similarly, the shape and dimensions of said elongate rod member or members are configured and adapted such that the rod member or rod members also does/do not interfere with any optional rotation of the dose setting wheel during injection, should the manufacturer of the pen injection system have configured the pen to function in such a way, for example, as with the Sanofi Solostar® or Flexpen® pen injection systems.

In accordance with another object, the elongate rod member or members is/are provided with a proximal extremity that is seated or fixed within a part of a holder body or housing of the injection monitoring system, for example through the provision of an enlarged proximal transverse cross-section at the proximal extremity of such an elongate rod member, and a correspondingly shaped recess having a reduced cross-sectional exit diameter provided in the body or housing of the injection monitoring system, preventing withdrawal of the elongate rod member from said housing.

Alternatively, and in accordance with yet another object, the at least one, or plurality of, elongate rod member(s), is/are integrally formed with the injection monitoring system holder.

Advantageously, and according to yet another object, the at least one, or plurality of, elongate rod member(s), is/are integrally formed with the activation cap of the injection monitoring system holder. The injection monitoring system is provided with a cap, on which the user presses to activate an injection, which cap encloses the magnetic field sensors within the injection monitoring system holder body or housing. According to this object therefore, the rod member or members extend(s) from the cap in a distal direction parallel to the central longitudinal axis, and also bypassing the hollow main body which contacts the dose setting wheel on the pen.

According to a still further object, the at least one, or plurality of, elongate rod member(s) comprise(s) at least one portion of said elongate rod member which defines an elliptical spline, extending in a distal direction from said injection monitoring system in parallel to the central longitudinal axis. By "elliptical spline", it is to be understood that whilst the elongate rod member extends in direction substantially in parallel to the central longitudinal axis, it is, according to said further object, defined at least in part along a length of the rod by an elliptical spline curve, that is to say, a curve similar to that of an arc of an ellipse, which extends towards the body of the pen injection system. Generally, the spline curve portion of the elongate rod member will be configured to maintain a sufficient distance between the elongate rod member and the body of the pen as the injection monitoring system is moved from the first monitoring position to the second monitoring position, and back again, such that the elongate rod member never comes into contact with an outer surface of the body of the injection pen system.

The elongate rod member is appropriately dimensioned, for example with a thickness of a corresponding material that makes the rod member semi-rigid along the length of the elongate rod member. Suitably appropriate materials for the elongate rod member are, for example, semi-rigid plastics materials such as mixtures of polycarbonate (PC) and acrylonitrile butadiene styrene (ABS) copolymer, commonly known as PC/ABS mixtures, although other suitable polymers and polymer mixtures providing suitable rigidity are generally known to the skilled person, and the elongate rod member can accordingly be made or constituted of any such suitably rigid material.

As has been mentioned above, the rotationally fixed coupling also comprises a sheath member comprising at least one runnel, or a plurality of runnels, configured and adapted to respectively receive the at least one, or the plurality of, elongate rod members, in sliding engagement. According therefore to another object, the at least one, or plurality of runnel(s) extend(s) in parallel to the central longitudinal axis. The runnel of the sheath member is aligned with the elongate rod member, such that the rod member is inserted into, and received by the runnel, during mounting of the injection monitoring module on the pen injection system. The runnel or runnels is/are generally shaped and dimensioned as a groove, having side walls, a base, and an opening, with the base and side walls of the groove being located in a lower surface of the sheath member, and the opening of the groove oriented to face the body of the injection pen system when the sheath member is mounted on the injection pen.

As is apparent from the preceding paragraph, the sheath member is mounted on the body of the injection pen system. According to yet another object therefore, the sheath member further comprises a body mount portion, configured and adapted to enable removable mounting of the sheath member to the body of the pen injection system. The body mount portion of the sheath member can comprise a wall of material, for example a plastics or polymer material such as polycarbonate (PC), acrylonitrile butadiene styrene (ABS) copolymer, or mixtures thereof known as PC/ABS mixtures, whereby the wall extends circumferentially around the body of the pen injection system, and is dimensioned to permit insertion of the pen body, into a bore formed by the circumferentially extending wall, and at the same time engage in elastic frictional engagement with the outer surface of said pen body, through suitable dimensioning of the bore of the sheath member. Optionally, and advantageously, the circumferentially extending wall is provided with a softer, more elastic, wall portion, for example, made of an elastomeric SEBS or similar elastomeric polymer, to engage with, and grip, a corresponding surface part of the body of the pen to prevent any undesired axial sliding movement of the pen within the bore of the circumferentially extending wall of the sheath member. Suitable elastomeric materials fulfilling this function are known per se in the art.

According to a still further object, the sheath member further comprises a retaining bridge configured and adapted to retain a respective at least one, or plurality of elongate rod member(s) in a corresponding respective at least one, or plurality of, runnel(s). The retaining bridge is generally located on an underside of the sheath member that is in contact with the outer surface of the body of the pen injection system when the injection monitoring module is mounted on the injection pen. The retaining bridge serves to maintain the elongate rod member in the corresponding runnel as the injection monitoring system is moved from the first monitoring position to the second monitoring position, and back again. The retaining bridge can be either integrally formed as part of the sheath member, or alternatively, can be provided as an insertable block to be seated, for example, by snap-fitting or ultrasound welding within a corresponding site configured to received said retaining bridge and situated on a lower surface of the sheath member opposite an opening of a corresponding runnel. In such a configuration, the retaining sheath member will allow a lower surface of the elongate rod member to slide against an upper surface of the retaining bridge, and retain the rod within the corresponding runnel of the sheath member. Alternatively, the retaining bridge can be formed via a suitable molding of the runnel, for example by providing the runnel with one or more mutually positioned projecting portions, or a shoulder, extending from a first inner wall surface of the runnel in the direction of a second and opposite inner wall surface of the runnel, and optionally along at least part of the length of the runnel. The retaining bridge thus formed thereby prevents the elongate rod member from accidentally falling out of the runnel as the elongate rod member slides along the runnel in parallel to the central longitudinal axis, when the injection monitoring system is moved from the first position to the second position, and vice-versa.

According to a yet further object, the rotationally fixed coupling further comprises a removable link configured and adapted to temporarily position the sheath member and the at least one, or plurality of, elongate rod members, in a predetermined, spaced apart relationship, along an axis parallel to central longitudinal axis during mounting of the injection monitoring module on the body of the injection pen system. The removable link serves to maintain the injection monitoring system with projecting elongate rod member, and the sheath member, as single mountable unit, connected to the hollow main body, in a predetermined spatial relationship during mounting of the monitoring module on the pen injection system, in order to avoid any accidental undesired axial displacement of the monitoring module when mounting the hollow main body on the dose setting wheel of the pen injection system. Accordingly, the removable link is configured to engage with, and retain, both a part of the housing or holder body of the injection monitoring system, and a part of the sheath member.

According therefore to another object, the sheath member and the injection monitoring system each comprise a recess configured to receive and engage in the temporary positioning relationship with a portion of the removable link.

The sheath member and holder body or housing of the injection monitoring system are thus provided, for example, with suitably shaped recesses for receiving a correspondingly complementary shaped projecting portion of the removable link. For example, a suitable complementary shape to engage with corresponding recesses provided on the sheath member and injection monitoring system housing can take the form of a butterfly wing, the wings extending either side of a central body which extends into, and defines, the predetermined space required for maintaining said sheath member and injection monitoring system in their respective positions when mounting the injection monitoring module on the injection pen system. The body of the butterfly can furthermore extend circumferentially around the holder body or housing of the injection monitoring system, and engage elastically therewith, in the manner of a cirtlip, or for example, more generally, a spring clip. The elastic engagement with the holder body of the injection monitoring system, and the butterfly wings engaging respectively in corresponding recesses in the sheath member and the body of the injection monitoring system, prevent the holder body of the injection monitoring system from being moved axially accidentally, thereby avoiding any untoward triggering of a false reading in the injection monitoring system. Once the injection monitoring module has been mounted, and the hollow main body correctly located on the dose setting wheel, of the injection pen system, the removable link is removed. In order to facilitate its reuse, for example, when removing the injection monitoring module from the injection pen system, the removable link is conveniently stored in a corresponding recess provided at another location on the sheath member, the recess having a diameter sufficient to retain the link, but permit its removal as and when required.

The hollow main body of the injection monitoring module comprises a central longitudinal bore with a proximal extremity and a distal extremity, the bore being dimensioned to permit coaxial mounting of the hollow main body onto, and around the body of the pen injection system. The hollow main body is appropriately made of any suitable material, for example of a durable polymer or plastic material, such as high density or high impact polypropylene, or alternatively, polycarbonate. Advantageously, the hollow main body is made of transparent, translucent, or opaque material, in order to enable a user to apprehend and recognise any visual cues, such as light emitting diodes, that might also be provided or integrated into the injection monitoring module, where such cues can be optionally used to indicate various states of operation of the injection monitoring system.

According therefore to another object, the hollow main body further comprises translational abutment means adapted and configured to prevent axial translational movement of the hollow main body along the central longitudinal axis, when the injection monitoring module is in the mounted position on the injection pen system. The translational abutment means defines the limit of axial translational movement of the hollow main body along the central longitudinal axis with respect to an activation button of the pen injection system, during mounting of the injection monitoring module on the pen injection system. Advantageously, and according to yet another object, the translational abutment means of the hollow main body comprises an annular flange extending inwardly into the bore toward the central longitudinal axis from an inside surface of the hollow main body. During mounting of the injection monitoring module on the injection pen system, the annular flange has a distal surface which comes into contact with a proximal facing surface of the activation button of the pen, thereby preventing any further translational movement of the hollow main body along the central longitudinal axis.

According to a still further object, the hollow main body further comprises a distal body portion which extends around and engages frictionally and elastically with an outer surface of the dose setting wheel. Such a distal body portion can extend substantially from the annular flange described in the previous paragraph, for example, or can be represented by a separately attachable hollow distal portion of the hollow main body, which is connectable to the hollow main body, for example via a socket and bayonet mount, or a screw-fit or snap-lock mount, and which is configured and dimensioned to have a bore that fits the dimensions of a dose setting wheel of an injection pen system. The frictionally elastic engagement can, for example, be provided via an appropriate elastomeric coating or deposit located on an inner circumferential surface of the distal portion of the hollow main body, for example in one or more zones, or alternatively as a continuous, contiguous, or semi-continuous/contiguous coating deposited on said inner circumferential surface of the distal portion of the hollow main body. The objective of such a frictionally elastic coating or deposit is to provide frictional grip between the distal body portion and the dose setting wheel in order to maintain correct positioning of the hollow distal body portion against the dose setting wheel. Appropriate types of elastomeric materials that can provide the correspondingly frictional engagement are known in the art per se, suitable elastomeric materials being, for example, SEBS.

As has been mentioned elsewhere in the present specification, the injection monitoring module comprises an injection monitoring system. Such a system comprises at least one or a plurality of magnetic sensors, the injection monitoring system being located substantially at, or adjacent, the proximal extremity of the bore of the hollow main body. The injection monitoring system will be described in further detail below, but basically, the injection monitoring system comprises a number of different components and means that provide for monitoring of an injection state, for example, such as:

initiation of an injection operation;
termination or end of an injection operation, whereby termination of an injection operation is to be understood to cover both a complete administration of a selected dose of substance to be injected, or discrete injection operations in which a user only injects a part of a dose, or causes a part of the selected dose to be ejected from the pen injection system.

Furthermore, in accordance with another object of the invention, the injection monitoring system is movable along the central longitudinal axis from a first monitoring position in which the injection monitoring system is not in abutting contact with a proximal surface of the injection activator, to a second monitoring position in which the injection monitoring system is in abutting contact with a proximal surface of the injection activator. The injection monitoring system is advantageously mounted at the proximal extremity of the bore of the hollow main body, and preferably completely covers, or at least substantially covers, said proximal extremity of the bore.

From the above, it will be understood that the injection monitoring system can be moved from an first position where there is no physical contact between the injection monitoring system and the activator button of the pen injection system, to a second position where physical contact is established between the monitoring system and the proximal surface of the injection activator of the pen injection system. Such movement will generally be a translational movement of the monitoring system along the central longitudinal axis from the first position to the second position. The injection monitoring module is configured so that rotation of the hollow main body and correspondingly coupled dose setting wheel, will result in the determination that the dose set or the dose dialled, is the dose that has been selected, because the injection monitoring system is locked against rotational movement around the central axis during dose setting. Determination of the beginning of an injection will also be effected through the detection of an increase in the magnetic norm as the injection monitoring system begins to translate along the central longitudinal axis from the first monitoring position towards the second monitoring position. When the monitoring system translates in a proximal direction, i.e. from the second monitoring position to the first monitoring position, thereby removing physical contact between the activator button of the pen injection system and the monitoring system, the injection monitoring system is configured to detect an end point of injection or ejection of injectable substance. One way of achieving this is to configure a reference point corresponding to the first monitoring position, and detect when the injection monitoring system has moved back to that reference point from any other point, using for example, an appropriately configured sensor.

The translational movement in the reverse direction to that of injection, i.e. translation of the monitoring system in a proximal direction back towards the user's hand or thumb, can suitably be provided by making use of the recoil energy of a biasing spring which is compressed during injection activation, and relaxed upon release of the activation button, and which can also be suitably provided in the bore and forming part of the injection monitoring system. After the activation cap has been released by the user, for example, by removal of thumb or finger pressure on the activation cap, either directly or indirectly, the recoil energy of the compressed biasing spring within the bore will move the injection monitoring system away from the activator button of the pen, biasing the injection monitoring system back to the first monitoring position.

According to another object of the invention, the injection monitoring module comprises a magnetic field producing means, located on or within the hollow main body, adjacent or at the proximal extremity of the central longitudinal bore. By the expression "located on or within the hollow main body", it is to be understood that the magnetic field producing means can be seated on a proximal facing surface of the hollow main body at the proximal extremity of the central bore, for example. Alternatively, and preferably, the magnetic field producing means can be seated within a cavity or recess provided in the hollow main body at, or adjacent, the proximal extremity of the central bore.

Various means for producing a magnetic field are known, for example, classical magnets, electromagnets, and mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;

composite materials consisting of a thermoplastic matrix and isotropic neodymium-iron-boron powder;

composite materials made up of a thermoplastic matrix and strontium-based hard ferrite powder, whereby the resulting magnets can contain isotropic, i.e. non-oriented, or anisotropic, i.e. oriented ferrite particles;

composite materials made of a thermo-hardening plastic matrix and isotropic neodymium-iron-boron powder;

magnetic elastomers produced with, for example, heavily charged strontium ferrite powders mixed with synthetic rubber or PVC, and subsequently either extruded into the desired shape or calendered into fine sheets;

flexible calendered composites, generally having the appearance of a brown sheet, and more or less flexible depending on its thickness and its composition. These composites are never elastic like rubber, and tend to have a Shore Hardness in the range of about 40 to about 70 Shore D ANSI. Such composites are generally formed from a synthetic elastomer charged with strontium ferrite grains. The resulting magnets can be anisotropic or isotropic, the sheet varieties generally having a magnetic particle alignment due to calendering;

laminated composites, generally comprising a flexible composite as above, co-laminated with a soft iron-pole plate;

neodymium-iron-boron magnets;

steels made of aluminium-nickel-cobalt alloy and magnetized;

alloys of samarium and cobalt.

Of the above list of magnetic field producing means suitable for use in the present invention, those selected from the group consisting of neodymium-iron-boron permanent magnets, magnetic elastomers, composite materials made up of a thermoplastic matrix and strontium-based hard ferrite powder, and composite materials made of a thermo-hardening plastic matrix and isotropic neodymium-iron-boron powder, are preferred. Such magnets are known for their ability to be dimensioned at relatively small sizes whilst maintaining relatively high magnetic field strength.

Whilst the magnetic field producing means can be of any suitable general shape, for example disk-shaped, including circular, ellipsoid, or any other suitable polygonal shape, it preferably has only a single dipole, with a single pair of diametrically opposing north and south magnetic poles. Although the magnetic field producing means can also optionally be substantially disk-shaped, such a disk-shape can also preferably include magnets which have an orifice substantially in the centre of the disk to form a ring or annular shaped magnet. Such a ring or annular shaped magnet can usefully be seated on a peripheral annular and proximal facing surface of the hollow main body at the proximal extremity thereof. Advantageously, and for the purposes of the presently envisaged configurations of the injection monitoring modules, the dipole magnets are rod-shaped or cylindrical dipole magnets, one positioned in opposite polar facing orientation with regard to other, for example N-S aligning with S-N, whereby the magnets are positioned to lay flat along their own longitudinal axes, across a horizontal plane that bisects, and is orthogonal to, the central longitudinal axis, each magnet being located on an opposing side of said central longitudinal axis, for example, at 180° of rotation around said central longitudinal axis, one with respect to the other.

The magnetic field production means is provided so that the magnetic field sensor will detect any changes in magnetic field, for example, due to rotational movement of the hollow main body relative to the magnetic sensor, during dose setting, thereby enabling the dialled dose set via the dose setting wheel to be determined.

The magnetic field sensor is used to measure the magnetic field produced by the magnetic field producing means. Movement of the hollow body and magnetic field production means around the central longitudinal axis relative to the rotationally fixed magnetic field sensor(s), as the dose wheel is rotated, is used to calculate or determine a dose of injectable substance in the injection pen system that has been dialled or set by the user. Once the dose has been set, activation of the proximal activator cap leading to translational movement of the injection monitoring system housing, and correspondingly housed magnetic field sensor(s) provided therewith, along the central longitudinal axis, is used to determine or calculate whether an injection has begun. Conversely, and respectively, when finger or thumb pressure on the proximal activator cap is released, the recoil energy in the biasing spring located within the injection monitoring system housing at a distal location of said housing causes the injection monitoring system to recoil, inducing translational movement of the injection monitoring system housing along the central longitudinal axis in a proximal direction, towards the thumb or fingers of the user, thereby also moving the magnetic field sensor(s) housed within the injection monitoring system in the proximal direction.

As indicated above, during injection, when digital pressure in a distal direction along the central longitudinal axis is being exerted on the housing of the injection monitoring system, the magnetic field sensor will detect changes in magnetic field due to the sensor translating along the longitudinal axis in a distal direction towards the magnetic field production means, and then in a reverse, proximal direction, as digital pressure is released from the injection monitoring system.

Furthermore, the compressive properties of the biasing spring, and the degree of resistance against distal movement of the injection monitoring system provided through said compressive properties, can be suitably used, to advantage, as a means for increasing the sensitivity of the monitoring system's detection of the begin point of an injection. For example, in the event of an uncontrolled distally oriented movement, where a user might suddenly push down on the activation cap of the monitoring module, it might be possible for an error to be induced in the injection monitoring system with regard to the beginning of an injection, due to the sudden increase in magnetic norm that would be detected by the magnetic field sensor. Due to the compressive properties of the biasing spring, such a rapid distal movement of the injection monitoring system, and corresponding induced increase in magnetic norm, is dampened to a level that the magnetic sensor can easily and unmistakably handle, thereby rendering determination of the injection point begin even safer and certain. To that extent, the biasing spring can be seen to represent more generally a dampening means for assisting in correct determination of the injection begin event.

With regard to the magnetic sensors in general, means for measuring magnetic fields to determine are known generally in the art. For example, magneto-resistors are a well known means. Such magneto-resistors are often designated by their abbreviations, e.g. AMR, GMR, TMR sensors, which designate the physical mechanisms by which these sensor components function. Giant magnetoresistance (GMR) is a quantum mechanical magnetoresistance effect observed in thin-film structures composed of alternating ferromagnetic and non-magnetic conductive layers. Anisotropic magnetoresistance, or AMR, is said to exist in materials in which a dependence of electrical resistance on the angle between the direction of electric current and direction of magnetization is observed. Tunnel magnetoresistance (TMR) is a magnetoresistive effect that occurs in a magnetic tunnel junction (MTJ), which is a component consisting of two ferromagnets separated by a thin insulator. Resistors that use these various properties are known per se.

In light of the above, the injection monitoring module and/or system according to the invention preferably uses one, or more, or a plurality of magnetometers as the one, more or plurality of magnetic field sensors. Such magnetometers differ from the GMR, AMR or TMR sensors in that it directly measures magnetic field strength. Magnetometers measure magnetic fields in two main ways: vector magnetometers measure the vector components of a magnetic field, and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field.

A preferred type of magnetometer therefore for use in the injection monitoring module according to the present invention is an ultra low-power high performance three axis Hall-effect magnetometer. Whilst it is possible for the magnetometer to be configured to measure magnetic field over three mutually perpendicular or orthogonal axes, it is preferred in the present case that the magnetic field sensors be configured to measure magnetic fields over just two of the three orthogonal axes, for example the X and Z axes.

As will be understood from the preceding paragraphs, and in accordance with yet another object, the injection monitoring module further comprises injection begin determination means. For example, the injection begin determination means are suitably represented by the magnetic field sensors, such as the one or more magnetometers located in the injection monitoring system and discussed elsewhere in the present specification. In order to detect the beginning of an injection therefore, the injection monitoring system, via the values measured and reported by the one or magnetometers present in the injection monitoring system, is configured to detect an increase in the magnetic norm, i.e. the magnetic field vector as determined along an axis running substantially parallel to, or coaxially with, the central longitudinal axis, in the absence of any accompanying affect on the magnetic field vector due to rotation of the injection monitoring system, as said injection monitoring system begins to move from the first monitoring position towards the second monitoring position.

Advantageously, and in accordance with a further object, the injection monitoring module comprises injection end determination means. The injection end determination can be contact-based, i.e. requiring physical or electrical contact or removal of such contact, between two surfaces, for example, in the manner of a mechanical or electrical switch, or alternatively can be based on contactless means, such as any number of known contactless detection means, for example wave-based sensors such as sound or light sensors or any other sensor applying the principles of a propagated waveform, and involving an emitter, a receiver and a optionally a reflecting surface, chemically or biologically reactive sensors, quantum effect sensors, etc, all generally known per se in the art.

Advantageously, and according to yet another object, the injection begin and/or end determination means comprise an optical sensor and a corresponding reflecting surface.

According to yet another object, the optical sensor is located on the injection monitoring system adjacent the at least one, or plurality of, elongate rod member(s). The optical sensor can be suitably located in the activation cap, for example, or alternatively, in the holder body or housing of the injection monitoring system. Advantageously, the optical sensor is positioned within the cap and/or the housing of the injection monitoring system, such that it can receive reflected light from a correspondingly and suitably located reflecting surface.

Accordingly, and further to another object, the reflecting surface for the optical sensor is located on the sheath member facing opposite to, and in optical axial alignment with, the optical sensor on the injection monitoring module.

The optical sensor and reflecting surface are therefore positioned such that reflected light coming from the reflecting surface travels to the optical sensor. The optical sensor is suitably configured to determine, for example, from the intensity of the reflected light, and/or the time taken for the reflected light to travel a path between the reflecting surface and the optical sensor, the distance that the optical sensor, and therefore a predetermined reference position in the injection monitoring system, has been moved, in parallel to, and along, the central longitudinal axis. The optical sensor is thus suitably equipped, for example, with a light emitting source, such as can be provided by a light emitting diode. The optical sensor can further be equipped with a focussing or diffusing system for such a light source, as is known per se, and in accordance with the properties of the reflecting surface, power of the light emitting source, etc, as is known per se in the art.

In injection pen systems in which the dose setting wheel rotates during injection, the end of an injection can be determined using the magnetic field vector values provided by the magnetic field sensors of the injection monitoring system, due to the fact that the magnetic field vector values registered by the magnetic sensors will vary depending, for example, on how many times the hollow main body comprising the magnets has rotated about the central longitudinal axis, coupled with the relative changes in magnetic field vectors linked to the distance of the magnetic sensors from the magnets. Such a configuration enables an end of injection event to be registered using only the magnetometers in this case.

However, in the case of injection pen systems in which the dose setting wheel does not rotate, for example, during injection, a contactless sensor as described above, e.g. the optical sensor, is particularly advantageous because the injection monitoring system is configured to use such an contactless sensor to signal when the injection monitoring device has returned via axial translation along the central longitudinal axis from the second injection monitoring position back to the first injection monitoring position, and therefore assign the injection end event to such a return position.

According to yet another object of the invention, the injection monitoring system comprises an electronic component board.

Advantageously, and according to a further object of the invention, the one or more or plurality of magnetic field sensors are electrically connected to the electronic component board. The one or more magnetic field sensors can helpfully be located on the electronic component board in diametrally opposed positions or otherwise radially distributed on the electronic component board, around the central longitudinal axis, and preferably, a single magnetic field sensor is located on the central longitudinal axis.

Even more advantageously, the electronic component board comprises an integrated control and data processing unit, such as at least one micro-controller, connected electrically to the one or more, or plurality, of magnetic field sensors, for processing information received from the magnetic field sensors. The electronic component board can therefore suitably be, for example, a printed circuit board of correspondingly appropriate dimensions. In the configurations envisaged in the present invention, such a printed circuit board is advantageously disk-shaped, with its centre corresponding to the point of intersection with the central longitudinal axis.

As has been mentioned above, the injection monitoring system comprises an optical sensor. Said optical sensor is, in accordance with yet another object, in electrical connection with the at least one micro-controller. The micro-controller controls the functioning of the optical sensor, and processes the signals and/or data received from the optical sensor to calculate, for example, the end of an injection sequence as described elsewhere in the present specification, and additionally, how far the injection monitoring system has translated along the central longitudinal axis. This information is used to calculate whether or not an injection has been completed.

The electronic component board is advantageously housed within the injection monitoring system housing or holder body that is located for the most part proximally of the hollow main body, and generally beyond the proximal extremity of the central bore. A distal part of the injection monitoring system housing is located within the bore. The injection monitoring housing is free to translate within the bore of the hollow main body, however, rotation is prevented due to the rotational stop means as embodied, for example, by the sheath member and elongate rod member.

Advantageously, the electronic component board is held such that a horizontal plane of the component board is located in a plane substantially orthogonal to said central longitudinal axis. The electronic component board is thus located in a fixed rotational relationship in the first injection monitoring position during dose setting relative to the hollow main body, so that rotation of the hollow main body does not cause corresponding rotation of the electronic component board. This means that when the hollow main body is rotated to "dial" or set the dose for injection, the at least one or more or plurality of magnetometers located on the electronic component board are prevented from rotating around the central longitudinal axis.

According to yet another object of the invention, the electronic component board comprises a communications unit in electrical connection with the at least one microcontroller. Such a communications unit can be one or more of any number of communications units known per se, such as a wireless communications unit, for example, Bluetooth®, Bluetooth LE® or any other short or long range wireless communication technologies.

According to still further object of the invention, the electronic component board comprises an autonomous, and optionally rechargeable, power supply, for example a lithium ion battery, which can be easily exchanged when depleted, or alternatively, a rechargeable battery, such as a rechargeable lithium ion battery. In the event that a rechargeable battery is provided, said rechargeable battery can be charged up when depleted via a corresponding charging port, such as a USB charging port, provided in the injection monitoring module and connected to the rechargeable battery. Both non-rechargeable, i.e. single-use batteries and rechargeable batteries are generally known per se to the skilled person. Advances in charging technology have today also made wireless charging a reality, and such a wirelessly chargeable battery, for example, using an induction charging system, is also foreseen as a possibility within the objects of the invention.

An integrated control and data processing unit, comprising at least one micro-controller, handles all electrical communication and signalling between the different electronic components of the electronic component board, including the magnetic field sensor(s) and optical sensor. It is also responsible for execution of the calculations enabling the precise positional location of the magnetic field sensor to be calculated and determined, as well as handling signals from an autonomous power supply and communication means integrated into the injection monitoring system, and which communicate with a local or remote data processing system, e.g. on a smartphone. Such integrated control and data processing units are known per se, and often integrate a central processing unit, a real time clock, one or more memory storage systems, and optionally communications systems or subsystems, along with other desired components.

These and other objects of the invention will become apparent and described in more detail in the following description relating to the figures and an example monitoring module.

BRIEF DESCRIPTION OF THE FIGURES

The invention will now be described in more detail with regard to the accompanying figures, provided for the purpose of illustration and exemplification, in which.

18

Figure 1:
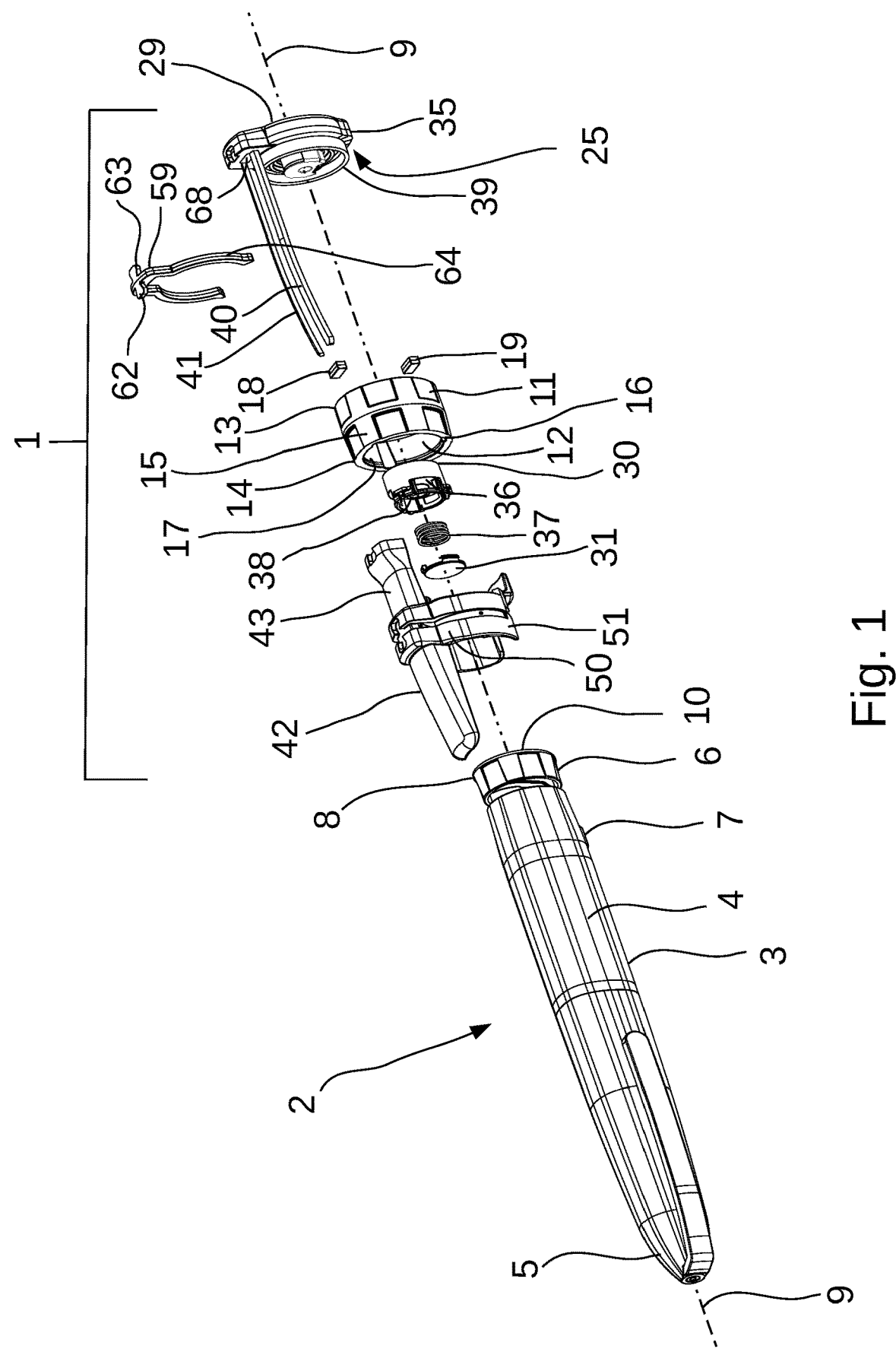
FIG. 1 is a schematic exploded perspective representation of an injection monitoring module to be mounted on a handheld pen injection system.
Figure 2:
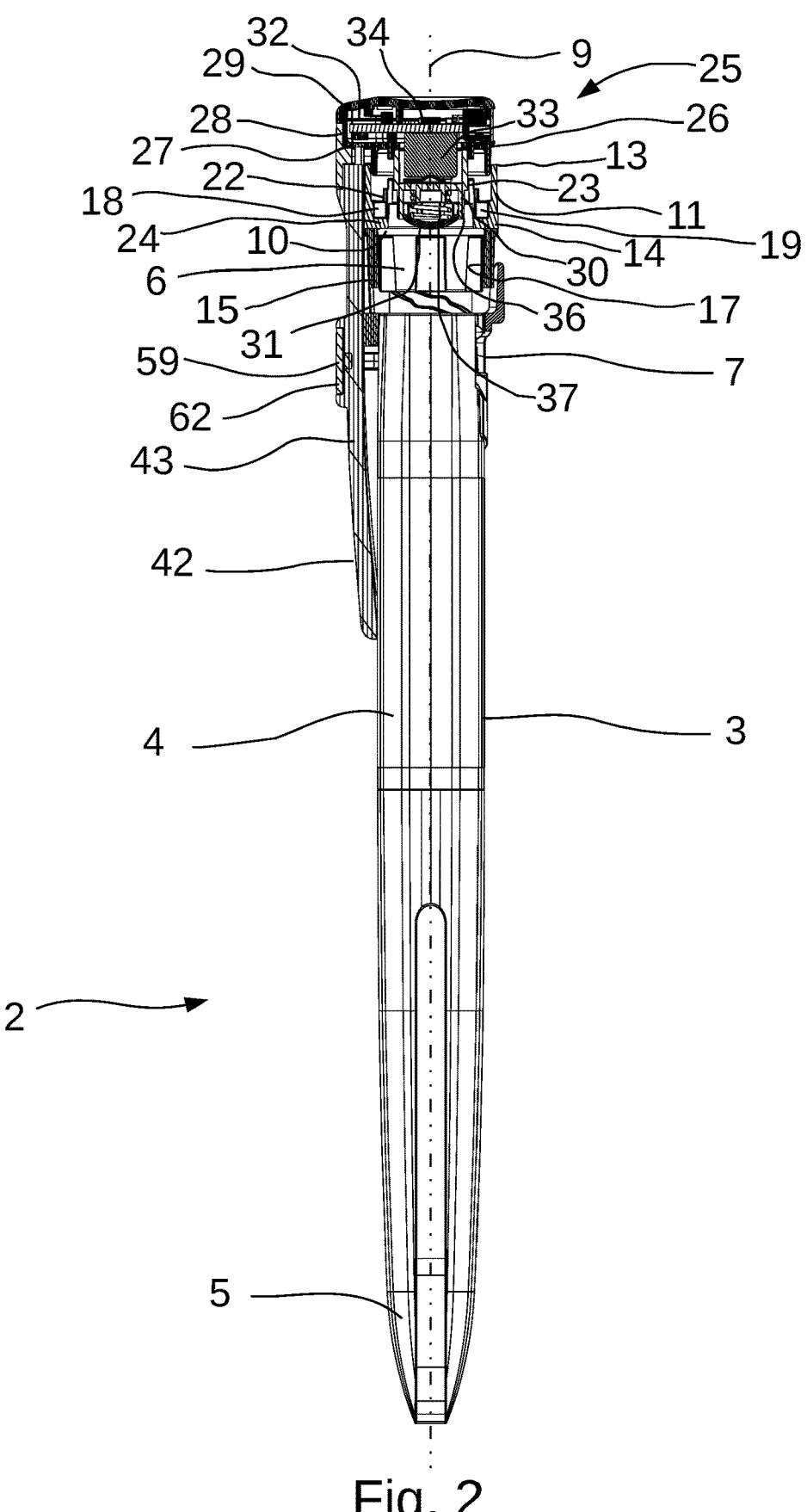
FIG. 2 is a schematic cross-sectional representation of the injection monitoring module of FIG. 1 mounted on a handheld pen injection system before use.
Figure 6:
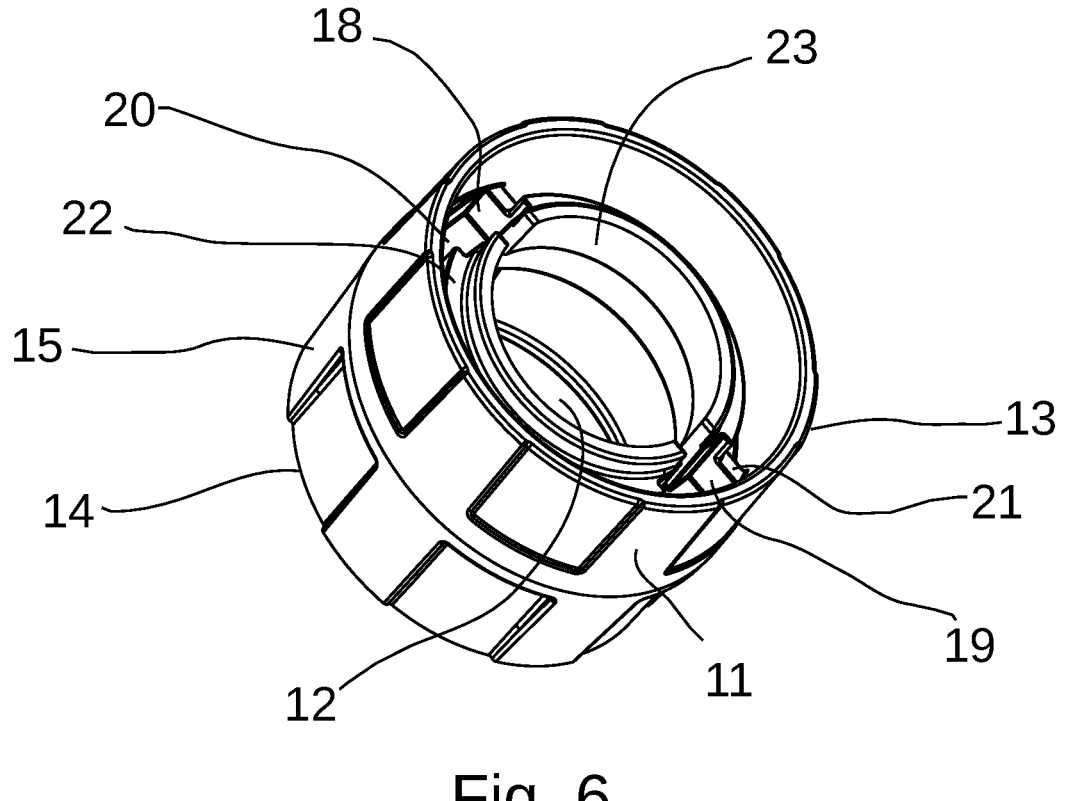

FIG. 6 is are schematic perspective representation of another detail of the injection monitoring module of FIG. 1 or FIG. 2.

DETAILED DESCRIPTION OF AN EXAMPLE

Turning now to FIGS. 1 and 2, a schematic representation of an injection monitoring module (1) according to the invention is shown. The injection monitoring module (1) is mounted on a handheld injection pen system (2), which comprises a pen injection system body (3) having an outer peripheral surface (4), a pen cap (5) covering the distal extremity of the pen injection system, a dose setting or dialling wheel (6), located at the proximal extremity of the pen injection system body (3), and a dialled dose visualisation window (7), located distally of the dose setting wheel (6), and displaying the dose which has been dialled by a user of the pen injection system. The injection monitoring module (1) according to the invention is mounted onto, covers and surrounds, a proximal extremity (8) of the injection pen system (2), and in particular is also mounted on the pen body (3) to at least partly cover and come into contact with the peripheral outer surface (4). The injection monitoring module (1) extends in a proximal direction beyond the proximal extremity (8) of the pen body (3) and in particular beyond the dose setting wheel (6). A central longitudinal axis (9) is also illustrated, which traverses the longitudinal axial centre of both the injection monitoring module (1) and the injection pen system body (3). The injection pen system (2) is provided with an activator button (10) proximally located from the dose setting or dialling wheel (6), as can be found in several commercially available injection pen systems. In the type of pen injection system (2) displayed in FIGS. 1 and 2, the dose setting wheel (6) is rotated about the central longitudinal axis (9) during dose setting, but is fixed against rotation during injection, i.e. the dose setting wheel doesn't rotate about the central longitudinal axis (9) during injection.

The injection monitoring module (1) comprises a hollow main body (11) which is dimensioned and sized to be coaxially mounted around the body (3) of the pen injection system (2). To this end, the hollow main body (11) comprises a central longitudinal bore (12) having a proximal extremity (13) and a distal extremity (14), and a central longitudinal axis that coincides with the central longitudinal axis (9). The hollow main body (11) further comprises a distal body portion (15) which extends around and frictionally engages with an outer surface of the dose setting wheel (6). Frictional engagement of the hollow main body (11) with the outer surface (4) of the dose setting wheel (6) can be achieved, for example by making the distal body portion out of an elastomeric frictional material (16), or alternatively by providing a coating of such an elastomeric frictional material on an inner peripheral surface (17) of the hollow main body, such elastomeric frictionally engaging materials being readily known in the art per se, to provide a push-fit or sliding-fit engagement of the distal portion (15) with the outer surface (4) of the pen body (3). A suitable elastomeric frictional material (16) for the distal body portion (15) can be a thermoplastic elastomer, such as SEBS or polystyrene-poly(ethylenebutylene)-polystyrene block copolymer, for example.

The hollow main body (11), illustrated in more detail in FIG. 6, extends in a proximal direction, above and beyond the limit of the activator button (10) of the pen injection system (2), such that the bore (12) houses both the dose setting wheel (6) and the activator button (10), and as illustrated in the Figures, within the distal body portion (15) of the hollow main body (11). The hollow main body (11) further comprises a magnetic field production means (18, 19) located on, or as illustrated in FIG. 6, in the bore (12) of the hollow main body (11). The magnetic field production means (18, 19) are suitably provided by a pair of single dipole magnets (18, 19), located diametrically opposite one to the other, each magnet respectively having a north (N) pole and a south (S) pole, with each pair of poles being preferably oriented in an upside down polar alignment across the central longitudinal axis, i.e. N-S/S-N, where the first magnet lies with a N-pole across a horizontal plane that is orthogonal to the central longitudinal axis, and the diametrically opposed magnet lies on the same plane orthogonal to the central longitudinal axis with a S-pole facing in the same planar orientation as the N-pole of the first magnet. The dipole magnets can be suitably formed into the shape of a rod, or a brick, or alternatively as a disk or ring, or any other suitable shape. The magnets are located in suitably dimensioned recesses (20, 21) provided in the hollow main body (11), the recesses (20, 21) being located at, or adjacent the proximal extremity (13) of the body (11). Alternatively, the magnetic field production means can be a single dipole ring shaped magnet, which is seated on a peripheral proximal surface or within a corresponding annular recess of the hollow main body (11) at the proximal extremity (13) of said hollow main body. It will be understood from the above that the magnetic field production means are free to rotate about the central longitudinal axis because the hollow main body (11) in which the magnets are positioned is itself mounted on, and in frictional engagement with, the dose setting wheel around said central longitudinal axis (9).

The hollow main body (11) further comprises an inner guide sleeve (22) located within the central longitudinal bore (12), and extending from an inner surface (17) of the hollow body (11) into the bore (12) via an annular flange portion (23), the sleeve (22) extending from an inward facing end of the flange (23) in a proximal direction towards the proximal extremity (13) of the hollow main body (11). The inner guide sleeve (23) receives and guides an injection monitoring system as will be described herein in more detail, as the injection monitoring systems translates within the bore (12) from a first monitoring position to a second monitoring position.

The hollow main body (11) also comprises translational abutment means (24) adapted and configured to prevent axial translational movement of the hollow main body (11) along the central longitudinal axis (9), when the injection monitoring module (1) is in the mounted position on the injection pen system (2). As illustrated in FIG. 2, the translational abutment means can comprise an annular flange (24) extending inwardly into the bore toward the central longitudinal axis from an inner surface (17) of the hollow main body. This annular flange (24) can advantageously be configured to be in abutting contact with a proximal facing surface of the distal body portion (15), thereby forming a distally facing surface on the annular flange which comes into abutment against the proximal facing surface of the activation button (10) of the pen injection system (2) when the injection monitoring module is mounted coaxially on the pen, prevent axial movement of the injection monitoring module in a distal direction.

Figure 3:
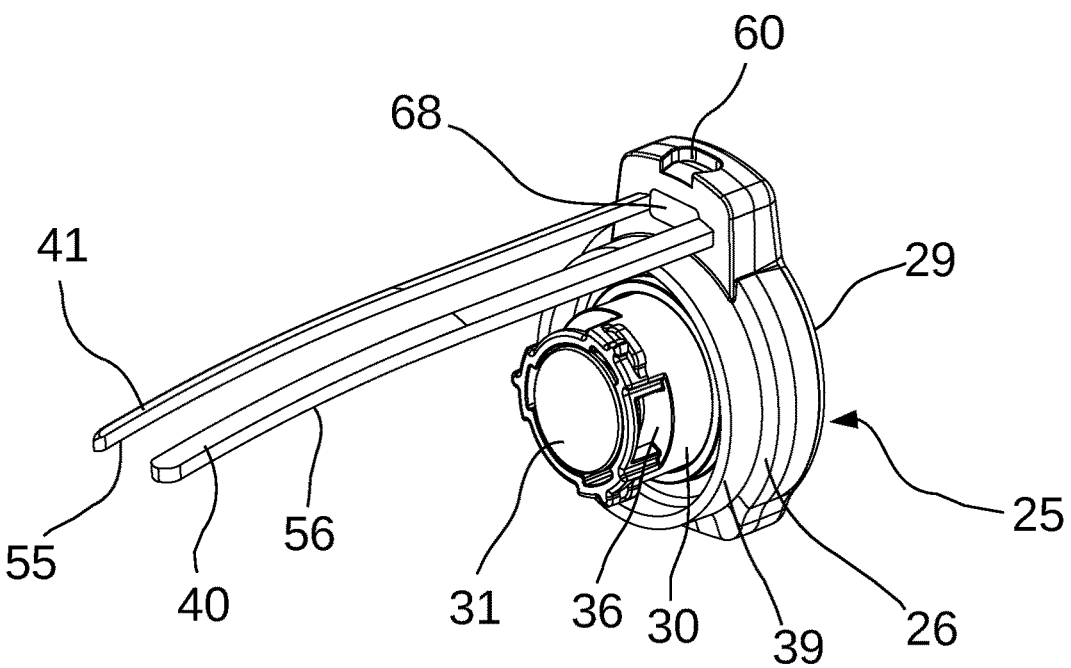
FIG. 3 is a schematic perspective representation of a detail of the injection monitoring module of FIG. 1 or FIG. 2.

As shown in FIGS. 1, 2 and 3, an injection monitoring system (25) is located at least partly in, and movable in translation within the bore (12) from a first monitoring position to a second monitoring position. The injection monitoring system (25) comprises several components, among which an injection monitoring system housing (26). The injection monitoring system housing (26) is shaped and configured to resemble a cup with a stem, with a base wall (27) extending over substantially the same, or similar diameter as the hollow main body, and substantially perpendicular to the central longitudinal axis (9), and a first wall (28) extending from an outer periphery of the base wall (27), in a proximal direction away from said base wall (27), thereby forming a cup shaped part with an inner volume that is closed by a proximal cap (29) forming an activator button, which is snap or push-fitted or adhered, or otherwise affixed onto said proximally extending first wall (28) at a proximal extremity of said first wall (28). The base wall (27) further comprises a second annular wall (30) extending from the base wall (27) in a distal direction from a location radially spaced apart from the central longitudinal axis (9), and having a diameter smaller than the diameter of the bore (12) of the hollow main body, enabling the housing (26) to move in translation within the sleeve (24) and bore (12) of the hollow main body (11). The second annular wall (30) is closed at its distal extremity by a flexible cross wall (31) to form the stem of the cup. The flexible cross wall can be made of, for example, a flexible membrane material, which is capable of deforming on contact with the activator button (10) of the pen injection system (2). The stem of the cup sits within the bore (12) of the hollow main body (11). The injection monitoring system housing (26), as defined by the cup shaped inner volume, receives and seats an electronic component board (32). The internal volume of the stem formed by the second annular wall (30) and the cross wall (31) receives an autonomous power supply (33), such as a single use, or rechargeable, battery, for example, a lithium ion battery electrically connected to the electronic component board (32) to provide power thereto. The electronic component board (32) is appropriately and generally a printed circuit board of suitable dimensions to be located within the internal volume of the cup formed by the base wall (27) and proximally extending first wall (28). The injection monitoring housing (26) optionally further comprises a light guide window, integrated into or being part of, the first wall (28), for example, a translucent, opaque, or transparent material shaped and with crystalline properties selected to guide a lightwave from the inside volume of the cup, for example, as produced by an optionally present light emitting diode or other lightwave producing component, to the outside of the injection monitoring system housing (26).

The electronic component board (32) further comprises at least one magnetometer (34), advantageously located on the central longitudinal axis (9), and in the case of a substantially circular shaped component board, substantially in the centre thereof so that it is coaxially aligned with the central longitudinal axis (9). In addition to the magnetometer (34), the injection monitoring system (25) also comprises an integrated control and data processing unit electrically connected to the magnetometer (34) for processing information received from the magnetometer. The integrated control and data processing unit handles all electrical communication and signalling between the different electronic components of the injection monitoring system. It is also responsible for execution of the dose management system and calculations enabling the precise positional location of the magnet to be calculated and determined, as well as handling signals from the autonomous power supply (33). The electronic component board can further be connected to a USB port (35), which can be configured as a power supply recharging port for a rechargeable battery (33), and/or be configured to enable basic setup of any programmable memory on the electronic component board, or to configure the data processing unit. The integrated control and data processing unit usually also comprises communication means which communicate with a local or remote data processing system, e.g. on a smartphone, such as a wireless communications circuit, for example, a Bluetooth® or BluetoothLE® wireless communications system, to name but two of many types of suitable communications means. The integrated control and data processing unit can suitably be programmed remotely, upon first use, or receive information and updates, in a similar way to other electronic devices today containing integrated control and data processing units, for example, wirelessly, or via any other suitable link, such as the USB port. Such integrated control and data processing units are known per se, and often integrate a central processing unit, a real time clock, one or more memory storage systems, and optionally communications systems or subsystems, along with other desired components. The electronic component board (32) is seated or located within the cup formed by the base wall (27) and first wall (28) of the injection monitoring system housing (26), substantially along the horizontal plane of the circuit board, i.e. generally orthogonal and perpendicular to the central longitudinal axis (9).

The second annular wall (30) further defines, with the cross wall (31), a chamber housing (36) for a biasing means (37) such as a compression spring, which biasing means (37) pushes against the cross wall (31) at the proximal end of the second annular wall (30), and which biasing means is constrained against a seating nub (38) at a proximal end of the chamber (36). The compression of the biasing means (37) causes the cross wall to flex in distal direction. The cross wall (31) is located at the distal extremity of the second annular wall (30) via snap or clip fit projections which lodge into corresponding recesses provided in the second annular wall (30). The biasing means (37) also serves as a dampener for the injection monitoring system (25), after a dose has been selected, when the injection monitoring system starts to move under digital pressure on the cap activation button, from the first monitoring position. The interplay of the compression spring, optionally assisted by the flexible cross wall, dampens the initial acceleration of the injection monitoring system (25) as it comes into contact with the activation button (10) on the injection pen (2). Given that the distance travelled between the first injection monitoring position and the second injection monitoring can be quite small, for example only a matter of a few tenths of a millimeter to a very few millimeters at most, depending on the dimensions of the injection pen, the biasing means not only accommodates the variations in axial geometry and molding tolerances of the various components of the various pens, but additionally facilitates detection of an increase in the magnetic norm, which magnetic norm increases as the magnetometer (34) in the injection monitoring system (25) is moved towards the magnets (18, 19) along the central longitudinal axis (9).

The injection monitoring housing (26) further comprises a third annular wall (39) extending from the base wall (27) at the periphery of said base wall (27) in a distal direction towards the hollow main body (11). This third annular base wall (36) provides further axial stabilisation for the injection monitoring system housing (26), in particular to the extent that it is dimensioned to be surrounded and guided by an inner peripheral circumference of the hollow main body (11) at the proximal extremity (13) thereof, both in the first monitoring position, and during activation of the activator button (10), in other words, during injection and/or ejection of a substance from the injection pen system (2), as well as during the return of the injection monitoring housing (26) from the second position to the first position.

Figure 4:
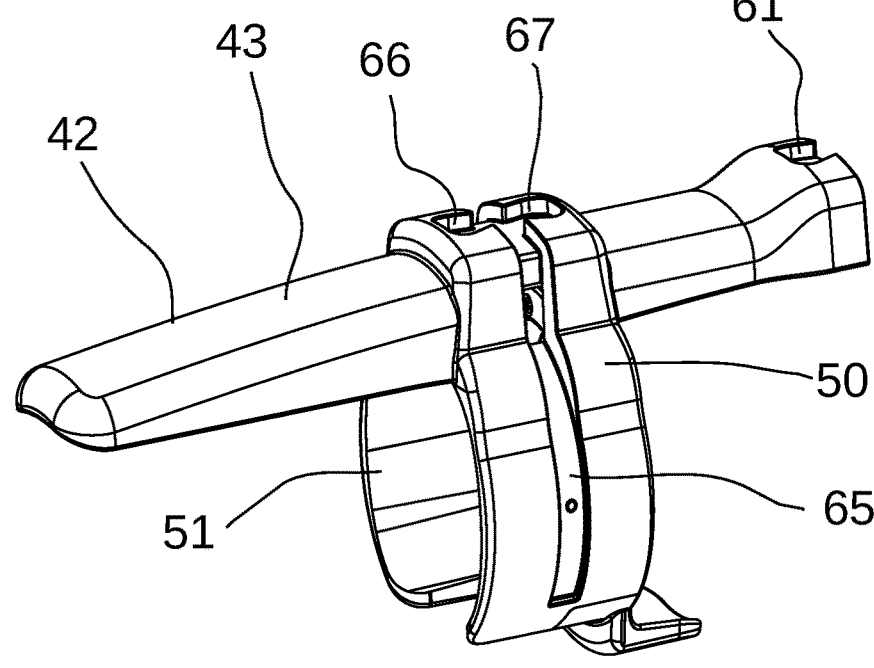
FIG. 4 is a schematic, perspective representations of another detail of the injection monitoring module of FIG. 1 or FIG. 2.

FIGS. 3 and 4 illustrate the various components of the rotational stop means, which are configured and adapted to prevent rotational movement of the injection monitoring system about said central longitudinal axis (9) during dose setting. The rotational stop means comprises a rotationally fixed coupling which is disposed in parallel to the central longitudinal axis (9). The rotationally fixed coupling connects the injection monitoring system (25) to the body (3) of the pen injection system (2) as will be described hereafter. The rotationally fixed coupling prevents rotation of the injection monitoring system (25) about the central longitudinal axis (9), not only during dose setting or dialling, but also more generally, during translation of the injection monitoring system (25) from the first monitoring position to the second monitoring position, and then translates back from the second monitoring position to the first monitoring position. In this way, it can be ensured that no rotation of the injection monitoring system (25) will occur, whether accidentally or deliberately, and in particular, not during dose selection or dose dialling where such rotation is the source of errors in determining a selected or dialled dose. The rotation stop means is furthermore configured and adapted to permit translational movement of the injection monitoring system, from the first injection monitoring position to the second injection monitoring position during injection, and vice-versa, that is to say, from the second injection monitoring position to the first injection monitoring position, whilst maintaining the rotational block. As will be apparent from the preceding description, the rotational stop means thus physically prevents rotation of the injection monitoring system (25) about the central longitudinal axis (9), whilst at the same time providing a translational guide system which corresponds to the permitted and configured translation the injection monitoring system (25) in both a distal and a proximal direction.

The rotationally fixed coupling comprises at least one elongate rod member (40, 41), or a plurality of elongate rod members (40, 41), as illustrated by the FIGS. 3, 4 and 5, extending from the injection monitoring system in a distal direction in parallel to the longitudinal axis and bypassing an outer surface of the hollow main body (11). Whilst the figures illustrate the presence of two elongate rod members, the rotationally fixed coupling can also comprise only a single elongate rod member located in an appropriate position.

The rotationally fixed coupling also comprises a sheath member (42), which mounted on the body (3) of the injection pen system (2), for example, via coaxial mounting around the pen body (3), for example, by sliding the sheath member (42) onto and along the pen body (3). The sheath member (42) is adapted and configured to receive the at least one (40, 41), or plurality of, elongate rod members (40, 41) in sliding engagement with said sheath member (42) during translational movement of the injection monitoring system (25) from the first monitoring position to the second monitoring position.

The elongate rod member (40, 41), and corresponding sheath (42), thus cooperate with each other to permit sliding engagement of the elongate rod member (40, 41) within the sheath member (42) as the injection monitoring system (25) is moved from the first injection monitoring position to the second injection monitoring position, but also vice-versa, that is to say, from the second injection monitoring position back to the first injection monitoring position. The sliding engagement between the elongate rod member (40, 41) and the sheath member (42) occurs substantially in parallel to the central longitudinal axis (9).

The at least one elongate rod member (40,41), or plurality of said elongate rod members (40, 41) extend from the injection monitoring system (25) in a distal direction, that is to say, in a direction away from the proximal extremities of both the injection pen system (25) and the injection monitoring module (1), and in parallel to the central longitudinal axis (9). Said rod member (40), or rod members (40, 41), is/are furthermore located outside of an outer surface of the hollow main body (11), and is/are shaped and dimensioned to bypass the hollow main body (11) on the outside thereof, and therefore does/do not interfere with the dose setting functionality of said hollow main body (11). This means that the hollow main body (11) can rotate without being hindered by the elongate rod member (40, 41), thereby allowing the hollow main body (11) to rotate and cause the dose setting wheel (6) to co-rotate, to enable a dose to be set on the pen injection system. Similarly, the shape and dimensions of the elongate rod member (40) or members (40, 41) are configured and adapted such that the rod member or rod members also does/do not interfere with any optional rotation of the dose setting wheel during injection, should the manufacturer of the pen injection system have configured the pen to function in such a way.

The elongate rod member or members (40, 41) is/are provided with a proximal extremity that is seated or fixed within a part of the injection monitoring system housing (26), for example through the provision of an enlarged proximal transverse cross-section at the proximal extremity of the elongate rod member (40, 41), and a correspondingly shaped recess having a reduced cross-sectional exit diameter provided in the injection monitoring system housing (26), thereby preventing withdrawal of the elongate rod member (40, 41) from said housing (26). Alternatively, the at least one, or plurality of, elongate rod member(s) (40, 41), is/are preferably integrally formed with the injection monitoring system housing (26), and in particular, is/are integrally formed with the activation cap (29) of the injection monitoring system housing (26). The cap (29) is accordingly configured and dimensioned so that it extends beyond the nominal diameter of the hollow main body (11). In this way, the elongate rod members (40, 41) are free to extend from the cap (29) in a distal direction parallel to the central longitudinal axis (9), and bypassing, without touching or coming into contact with, the hollow main body (11).

The at least one, or plurality of, elongate rod member(s) (40, 41) further comprise(s) at least one portion which defines an elliptical spline, extending in a distal direction from the cap (29) in parallel to the central longitudinal axis (9). The "elliptical spline" shape of the elongate rod members facilitate contact-free passage of the rod around the relatively enlarged diameter of the hollow main body, whilst at the same time reducing the need for increasing the diameter of the injection monitoring system housing (26). The spline curve portion of the elongate rod member (40, 41) is thus configured to maintain a sufficient distance between the elongate rod member (40, 41) and both the hollow main body (11) and the body of the pen (3) as the injection monitoring system (25) is moved from the first monitoring position to the second monitoring position, and back again, such that the elongate rod member (40, 41) preferably never comes into contact with an outer surface (4) of the body of the injection pen system.

The elongate rod member (40, 41) is furthermore appropriately dimensioned, for example with a thickness of a corresponding material that makes the rod member (40, 41) semi-rigid along the length of the elongate rod member (40, 41). Suitably appropriate materials for the elongate rod member are, for example, semi-rigid plastics materials such as mixtures of polycarbonate (PC) and acrylonitrile butadiene styrene (ABS) copolymer, commonly known as PC/ABS mixtures, although other suitable polymers and polymer mixtures providing suitable rigidity are generally known to the skilled person, and the elongate rod member can accordingly be made or constituted of any such suitably rigid material.

The sheath member (42) comprises a generally elongate and flat body (43), which extends in parallel with, and generally espouses the shape of the outside surface (4) of the pen body (3). The sheath member (42) further comprises at least one runnel (44), or a plurality of runnels (44, 45), configured and adapted to respectively receive the at least one, or the plurality of, elongate rod members (40, 41), in sliding engagement. The at least one, or plurality of runnel (s) (44,45) also extend(s) in parallel to the central longitudinal axis (9). The runnel (44, 45) of the sheath member (42) is axially aligned with the elongate rod member (40, 41), such that the rod member (40, 41) is inserted into, and received by the runnel (44, 45), during mounting of the injection monitoring module (1) on the pen injection system (2). The runnel (44) or runnels (44, 45) is/are generally shaped and dimensioned as a groove, having side walls (46, 47), a base (48), and forming an opening, with the base (48) and side walls (46, 47) of the groove being located in a lower surface (49) of the sheath member (42). The opening of the runnel (44, 45) is oriented to face the body (3) of the injection pen system (2) when the sheath member (42) is mounted on the injection pen body (3).

In order to locate the sheath member (42) appropriately on the outer surface (4) of the body (3) of the injection pen (2), the sheath member further comprises a body mount portion (50), configured and adapted to enable removable mounting of the sheath member to the body (3) of the pen injection system (2). The body mount portion (50) thus comprises a wall (51) of material, for example a plastics or polymer material such as polycarbonate (PC), acrylonitrile butadiene styrene (ABS) copolymer, or mixtures thereof known as PC/ABS mixtures, whereby the wall (51) extends circumferentially around the body (3) of the pen injection system (2), and is dimensioned to permit insertion of the pen body, into a bore (52) formed by the circumferentially extending wall (51), and at the same time engage in elastic frictional engagement with the outer surface (4) of said pen body (3), through suitable dimensioning of the bore (52). The circumferentially extending wall (51) is advantageously provided with a softer, more elastic, wall portion (53), for example, made of an elastomeric SEBS or similar elastomeric polymer, to engage with, and grip, a corresponding surface part (4) of the body (3) of the pen (2) to prevent any undesired axial sliding movement of the pen within the bore (52) of the circumferentially extending wall (51).

The sheath member can further be provided with a retaining bridge (54) configured and adapted to retain a respective the at least one, or plurality of elongate rod member(s) (40, 41) in the corresponding respective at least one, or plurality of, runnel(s) (44, 45). The retaining bridge (54) is generally located on an underside of the body (43) sheath member (42) that is in contact with the outer surface (4) of the body (3) of the pen injection system (2) when the injection monitoring module (1) is mounted on the injection pen (2). The retaining bridge (54) serves to maintain the elongate rod member (40, 41) in the corresponding runnel (44, 45) as the injection monitoring system (25) is moved from the first monitoring position to the second monitoring position, and back again. The retaining bridge (54) can be either integrally formed as part of the body (43) of sheath member (42), or alternatively, can be provided as an insertable block to be seated, for example, by snap-fitting or ultrasound welding within a corresponding site configured to receive said retaining bridge and situated on a lower surface (49) of the sheath opposite an opening of a corresponding runnel (44, 45). In such a configuration, the retaining sheath (54) will allow a lower surface (55, 56) of the elongate rod member (40, 41) to slide against an upper surface (57, 58) of the retaining bridge (54), and retain the rod (40, 41) within the corresponding runnel (44, 45), of the sheath member (42). Alternatively, the retaining bridge (54) can be formed via a suitable molding of the runnel (44, 45), for example by providing the runnel (44, 45) with one or more mutually positioned projecting portions, or a shoulder, extending from a first inner wall surface (46) of the runnel in the direction of a second and opposite inner wall surface (47) of the runnel, and optionally along at least part of the length of the runnel (44, 45). The retaining bridge (54) prevents the elongate rod member (40, 41) from accidentally falling out of the runnel (44, 45) as the elongate rod member (40, 41) slides along the runnel (44, 45) in parallel to the central longitudinal axis (9), when the injection monitoring system (25) is moved from the first position to the second position, and vice-versa.

The rotationally fixed coupling further comprises a removable link (59) configured and adapted to temporarily position the sheath member (52) and the at least one, or plurality of, elongate rod members (40, 41), in a predetermined, spaced apart relationship, along an axis parallel to central longitudinal axis (9) during mounting of the injection monitoring module (1) on the body (3) of the injection pen system (2). The removable link serves to maintain the injection monitoring system (25) with projecting elongate rod member (40, 41), and the sheath member (42), as a single mountable unit, connected to the hollow main body (11), in a predetermined spatial relationship during mounting of the monitoring module (1) on the pen injection system (2), in order to avoid any accidental undesired axial displacement of the monitoring module (1) when mounting the hollow main body (11) on the dose setting wheel (6) of the pen injection system (2). Accordingly, the removable link is configured to engage with, and retain, both a part of the injection monitoring system housing (26), and a part of the sheath member (42).

Accordingly, the sheath member (42) and the injection monitoring system (25) each comprise a recess (60, 61), configured to receive and engage in the temporary positioning relationship with a portion of the removable link. The recess (60) of the injection monitoring system is provided in a peripheral area of the cap (29), whereas the recess of the sheath member is provided at a proximal extremity of the body (43) of the sheath member (42), the two recesses being axially aligned in parallel to the central longitudinal axis (9), one with the other, when the removable link (59) is inserted into the recesses (60, 61).

The removable coupling link (59) comprises a correspondingly complementary shaped projecting portion (62, 63). For example, a suitable complementary shape to engage with corresponding recesses (60, 61) provided on the sheath member (42) and injection monitoring system housing (26) can take the form of a butterfly wing, the wings (62, 63) extending either side of a central body (64) which extends into, and defines, the predetermined space required for maintaining said sheath member (42) and injection monitoring system housing (26) in their respective positions when mounting the injection monitoring module (1) on the injection pen system (2). The body (64) of the butterfly can furthermore extend circumferentially around the injection monitoring housing (26), and engage elastically therewith, in the manner of a circlip, or for example, more generally, a spring clip. The elastic engagement with the injection monitoring system housing (26), and the butterfly wings (62, 63) engaging respectively in corresponding recesses (60, 61) in the sheath member (42) and the housing body (26) prevent the housing body (26) from being moved axially accidentally, thereby avoiding any untoward triggering of a false reading in the injection monitoring system (25). Once the injection monitoring module (1) has been mounted on the pen (2), and the hollow main body (11) correctly located on the dose setting wheel (6), the removable link (59) is removed. In order to facilitate its reuse, for example, when removing the injection monitoring module (1) from the injection pen system (2), the removable link (59) is conveniently stored in a corresponding recess (65, 66, 67) provided at another location on the sheath member (42), for example, at or adjacent, the mounting portion (51) of the sheath member (42), wherein the recess (65) will have a diameter sufficient to retain the removable link (59), but permit its removal as and when required.

Figure 5A:
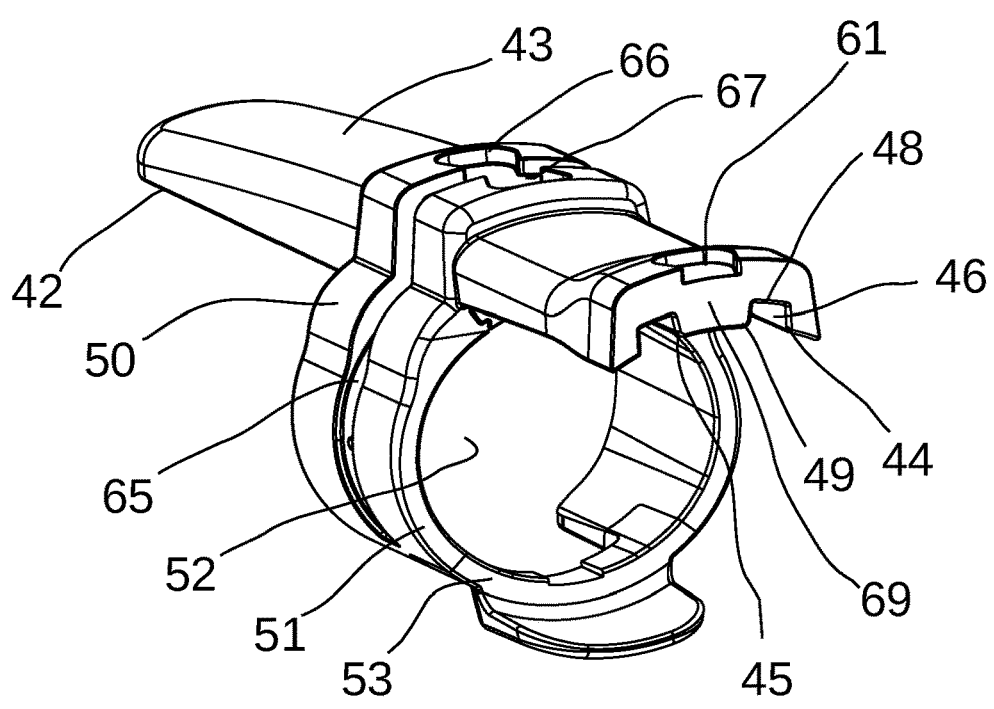
FIGS. 5A and 5B are schematic, perspective representations of the detail of FIG. 4 viewed from different angles.
Figure 5B:
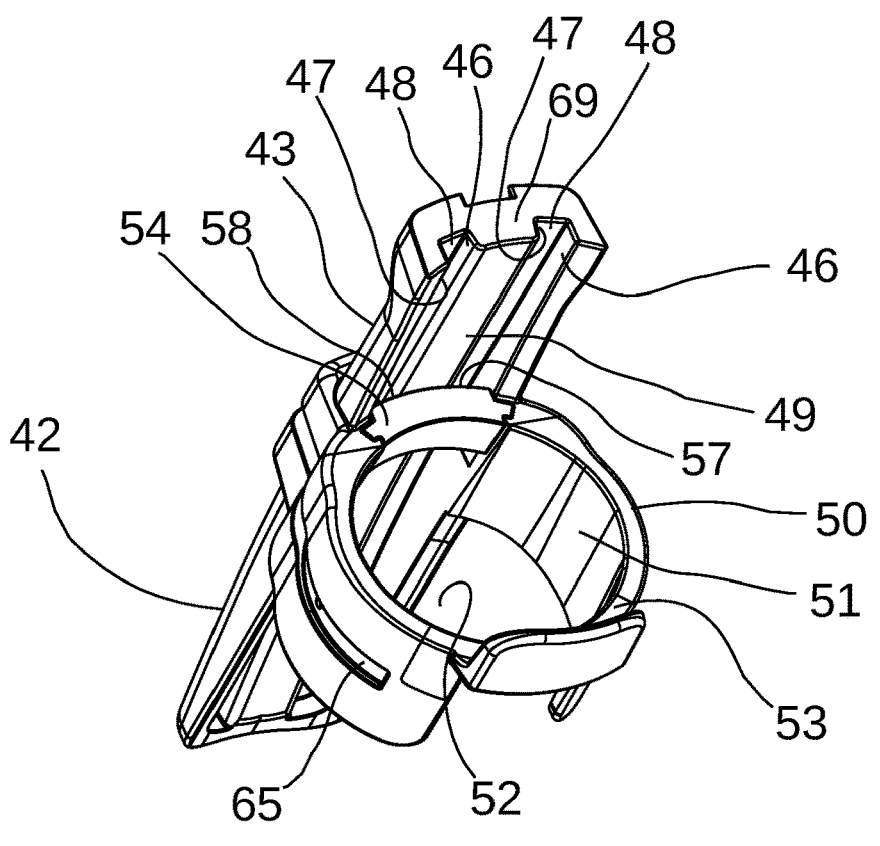

FIGS. 3, 5A, 5B illustrate another particular aspect of the injection monitoring module (1) in which an optical sensor (68), as an appropriate example of a contactless sensor, is present. The optical sensor (68) is located on the injection monitoring system housing (26) adjacent the at least one, or plurality of, elongate rod member(s) (40, 41), and as illustrated in FIG. 3 is suitably located in the activation cap (29) portion of the housing (26). In this embodiment, the optical sensor (68) is positioned between the two elongate rod members (40, 41), such that it can receive reflected light from a correspondingly and suitably located reflecting surface (69) located at the proximal extremity of the body (43) of the sheath member (42). The optical sensor (68) and reflecting surface (69) are therefore positioned such that reflected light coming from the reflecting surface (69) travels to the optical sensor (68). The optical sensor (68) is suitably configured to determine, for example, from the intensity of the reflected light, and/or the time taken for the reflected light to travel a path between the reflecting surface (69) and the optical sensor (68), the distance that the optical sensor (68), and therefore a predetermined reference position in the injection monitoring system (25), has been moved, in parallel to, and along, the central longitudinal axis. The optical sensor (68) is thus suitably equipped, for example, with a light emitting source, such as can be provided by a light emitting diode. The optical sensor (68) can further be equipped with a focussing or diffusing system for such a light source, as is known per se, and in accordance with the properties of the reflecting surface (69), power of the light emitting source, etc, as is known per se in the art, with regard to the functioning and operation of such light sensors.

In operation, the monitoring module functions according to the following brief description, after mounting and correct positioning of the monitoring module (1) onto the body (1) of the injection pen. The removable link (59) that initially holds the hollow main body, injection monitoring system, elongate rod members (40, 41), and sheath member (42) together, is removed, and optionally placed in the corresponding recesses (65, 66, 67). A dose is set by rotating the hollow main body, which causes the dose setting wheel to corotate. As the elongate rod members (40, 41) are already engaged in the runnels of the sheath member (42), the injection monitoring housing (26) is prevented from rotating within the bore (12) of the hollow main body. The monitoring system (25) then only receives signals from the magnetometers that correspond to the actual dose selected by rotation of the dose setting wheel (6). Without the rotational lock provided in the injection monitoring module of the invention, inadvertent relative rotations could cause errors in these readings, which would require supplementary corrective measures in order to attempt to determine whether the dose dialled was actually the dose selected. The dose set or dialled having been validated as the selected dose by the processing unit, the monitoring system now determines whether an injection operation has begun, i.e. whether or not the injection monitoring system has begun to be translated along the central longitudinal axis (9) from the first monitoring position to the second monitoring position. This is achieved when the magnetometers signal an increase in the magnetic norm to the processing unit, as an increase in the magnetic norm is synonymous with a movement of the magnetometer towards the magnets. In this way, the monitoring system knows that an injection operation has begun. In injection pens that cause the dose wheel to rotate upon injection, an injection end point can be calculated similarly using magnetic field vector values captured by the magnetometer. However, in pens where the dose setting wheel does not rotate, it is normally impossible to know when an injection has ended, since a user might leave the injection monitoring system (25) in contact with the injection activation button (10 of the pen (2) for an indeterminate period, or barely in contact with the activation button (10). A measurement of time elapsed in the second monitoring position would therefore be potentially fraught with errors requiring correction. In such a configuration therefore, the optical sensor is used to provide a reference point for the injection monitoring system, and the optical sensor therefore determines when the injection monitoring system has returned from the second monitoring position to the reference point of the first monitoring position, thereby signalling an injection end point.

Thus, as will be understood from what precedes, the present injection monitoring module makes it possible to determine with certainty that the dialled dose is indeed the selected dose, the point at which an injection begins, and the point at which an injection ends in a significantly more efficient manner than was previously the case.

The invention claimed is:

1. Injection monitoring module adapted and configured to be removably mounted to a proximal extremity of an injection pen system for delivery of a drug, the injection pen system having a pen body, a proximally located dose setting wheel connected to said body, and an injection activator, the dose setting wheel being rotatable about a central longitudinal axis of the pen injection system during dose setting, wherein the injection monitoring module comprises:

a hollow main body adapted and configured to be coaxially mounted on, and engage in corotation with, the dose setting wheel at the proximal extremity of the injection pen system, the hollow main body comprising a central longitudinal bore having a proximal extremity and a distal extremity, and a central longitudinal axis;

a magnetic field production means, located on or within the hollow main body, at the proximal extremity of the central longitudinal bore;

an injection monitoring system comprising at least one or a plurality of magnetic sensors, the injection monitoring system being located at the proximal extremity of, and movable in translation along said central longitudinal axis within the bore of the hollow main body, from a first monitoring position in which the injection monitoring system is not in abutting contact with a proximal surface of the injection activator, to a second monitoring position in which the injection monitoring system is in abutting contact with a proximal surface of the injection activator;

the injection monitoring module further comprising a rotational stop means configured and adapted to prevent rotational movement of the injection monitoring system about said central longitudinal axis during dose selection.

2. Injection monitoring module according to claim 1, wherein the rotational stop means comprises a rotationally fixed coupling disposed in parallel to the central longitudinal axis, the rotationally fixed coupling connecting the injection monitoring system to the body of the pen injection system.

3. Injection monitoring module according to claim 1, wherein the rotational stop means is further configured and adapted to permit translational movement of the injection monitoring system from the first injection monitoring position to the second injection monitoring position during injection, and vice-versa, from the second injection monitoring position to the first injection monitoring position, after completion of injection.

4. Injection monitoring module according to claim 2, wherein the rotationally fixed coupling comprises:

at least one elongate rod member, or a plurality of elongate rod members, extending from the injection monitoring system in a distal direction in parallel to the longitudinal axis and bypassing an outside surface of the hollow main body; and a sheath member, mounted on the body of the injection pen system, adapted and configured to receive the at least one, or plurality of, elongate rod members in sliding engagement with said sheath member during translational movement of the injection monitoring system from the first monitoring position to the second monitoring position.

5. Injection monitoring module according to claim 4, wherein the at least one, or plurality of, elongate rod member(s), of the rotationally fixed coupling of the rotational stop means is/are integrally formed with an injection monitoring system holder.

6. Injection monitoring module according to claim 4, wherein the at least one, or plurality of, elongate rod member(s), is/are integrally formed with a cap of the injection monitoring system holder.

7. Injection monitoring module according to claim 4, wherein the at least one, or plurality of, elongate rod member(s) comprises at least one portion of the elongate rod member which defines an elliptical spline, extending in a distal direction from said injection monitoring system in parallel to the central longitudinal axis.

8. Injection monitoring module according to claim 4, wherein the sheath member comprises at least one runnel, or a plurality of runnels, configured and adapted to respectively receive the at least one, or the plurality of, elongate rod members, in sliding engagement.

9. Injection monitoring module according to claim 8, wherein the at least one, or plurality of runnel(s) extend(s) in parallel to the central longitudinal axis.

10. Injection monitoring module according to claim 4, wherein the sheath member further comprises a body mount portion, configured and adapted to enable removable mounting of the sheath member to the body of the pen injection system.

11. Injection monitoring module according to claim 4, wherein the sheath member further comprises a retaining bridge including at least one, or plurality of, runnel(s) each of which being configured to retain one of said at least one, or plurality of elongate rod member(s).

12. Injection monitoring module according to claim 4, wherein the rotationally fixed coupling further comprises a removable link configured and adapted to temporarily position the sheath member and the at least one, or plurality of, elongate rod members, in a predetermined, spaced apart relationship, along an axis parallel to central longitudinal axis during mounting of the injection monitoring module on the body of the injection pen system.

13. Injection monitoring module according to claim 4, wherein the sheath member and the injection monitoring system each further comprise a recess configured to receive and engage in a temporary positioning relationship with a portion of the removable link.

14. Injection monitoring module according to claim 1, wherein the hollow main body further comprises translational abutment means adapted and configured to prevent axial translational movement of the hollow main body along the central longitudinal axis, when the injection monitoring module is in the mounted position on the injection pen system.

15. Injection monitoring module according to claim 14, wherein the translational abutment means of the hollow main body comprises an annular flange extending inwardly into the bore toward the central longitudinal axis from an inside surface of the hollow main body.

16. Injection monitoring module according to claim 1, wherein the hollow main body further comprises a distal body portion which extends around and frictionally engages with an outer surface of the dose setting wheel.

17. Injection monitoring module according to claim 1, wherein the injection monitoring module further comprises injection begin determination means or injection end determination means and the injection begin and/or end determination means comprise an optical sensor and a corresponding reflecting surface.

18. Injection monitoring module according to claim 4, wherein an optical sensor is located on the injection monitoring system adjacent the at least one, or plurality of, elongate rod member(s) and the reflecting surface for the optical sensor is located on the sheath member facing opposite to, and in optical axial alignment with, the optical sensor on the injection monitoring module.

19. Injection monitoring module according to claim 18, wherein the injection monitoring system further comprises an electronic component board, and at least one microcontroller, in electrical connection with the one or plurality of magnetic field sensors and the at least one micro-controller is in electrical connection with the optical sensor.

20. Injection monitoring module according to claim 19, wherein the electronic component board comprises a communications unit in electrical connection with the at least one microcontroller.

21. Injection monitoring module according to claim 18, wherein the electronic component board comprises an autonomous power supply.

* * * * *